(12) United States Patent
Kaye et al.

(10) Patent No.: US 9,116,121 B2
(45) Date of Patent: Aug. 25, 2015

(54) SECOND GENERATION LOW-COST PARTICLE COUNTER

(75) Inventors: Paul Henry Kaye, Hertfordshire (GB); Edwin Hirst, Hertfordshire (GB)

(73) Assignee: UH Ventures Limited, Hartfield (GB)

( * ) Notice: Subject to any disclaimer, the term of this patent is extended or adjusted under 35 U.S.C. 154(b) by 249 days.

(21) Appl. No.: 13/881,570

(22) PCT Filed: Oct. 19, 2011

(86) PCT No.: PCT/GB2011/052028
§ 371 (c)(1),
(2), (4) Date: May 20, 2013

(87) PCT Pub. No.: WO2012/056217
PCT Pub. Date: May 3, 2012

(65) Prior Publication Data
US 2013/0229655 A1  Sep. 5, 2013

(30) Foreign Application Priority Data
Oct. 26, 2010 (GB) .................................. 1018046.1

(51) Int. Cl.
*G01N 21/51* (2006.01)
*G01N 15/02* (2006.01)
(Continued)

(52) U.S. Cl.
CPC ............ *G01N 21/51* (2013.01); *G01N 15/0205* (2013.01); *G01N 15/1434* (2013.01);
(Continued)

(58) Field of Classification Search
CPC .......... G01N 15/0205; G01N 15/1434; G01N 15/1486; G01N 15/1493; G01N 21/51; G01N 15/02; G01N 15/14; G01N 21/47
USPC ................................................. 356/335–344
See application file for complete search history.

(56) References Cited

U.S. PATENT DOCUMENTS 3,826,364 A * 7/1974 Bonner et al. ................ 209/3.1
3,873,204 A * 3/1975 Friedman et al. ............. 356/39
(Continued)

OTHER PUBLICATIONS

United Kingdom Intellectual Property Office, Patents Act 1977: Search Report under Section 17, Application No. GB1018046.1, dated Jan. 25, 2011 (1 page).
(Continued)

*Primary Examiner* — Kara E Geisel
*Assistant Examiner* — Jarreas C Underwood
(74) *Attorney, Agent, or Firm* — Wood, Herron & Evans, LLP

(57) ABSTRACT

An apparatus for the detection of a fluid-borne particle (10) in an optically defined particle sensing zone, the apparatus comprising: i) a scattering chamber (40); ii) a means for providing a sample of fluid (34), containing the fluid-borne particle, in the form of a flow through the optically defined particle sensing zone; iii) A means for generating a beam of radiation (12) through the optically defined particle sensing zone; iv) a single reflector or refractor (14) means having a primary focus (16) within the optically defined particle sensing zone and a secondary focus (20) located outside the beam of radiation; v) a detector means comprising a first photosensitive detection area (26) a second photosensitive detection area (29); vi) a means for deriving area from the radiation detected by the first photosensitive detection area and second photosensitive detection area of the detection means wherein the single reflector or refractor means is adapted to direct radiation scattered from the fluid borne particle passing through the beam of radiation within the optically defined particle sensing zone to the detection means located at the secondary focus of the single reflector or refractor means and the optically sensing zone comprises a first and a second zone.

24 Claims, 8 Drawing Sheets

(51) Int. Cl.
　　*G01N 15/14*　　(2006.01)
　　*G01N 21/47*　　(2006.01)
　　*G01N 1/22*　　(2006.01)

(52) U.S. Cl.
　　CPC ........ *G01N21/47* (2013.01); *G01N 2001/2223* (2013.01); *G01N 2015/1486* (2013.01); *G01N 2015/1493* (2013.01)

(56) References Cited

U.S. PATENT DOCUMENTS

| | | | | |
|---|---|---|---|---|
| 4,140,395 | A | * | 2/1979 | Kreikebaum ................ 356/336 |
| 4,422,761 | A | * | 12/1983 | Frommer ..................... 356/338 |
| 5,416,580 | A | * | 5/1995 | Trainer ....................... 356/336 |
| 5,467,189 | A | * | 11/1995 | Kreikebaum et al. ........ 356/336 |
| 5,870,190 | A | | 2/1999 | Unger |
| 6,198,110 | B1 | * | 3/2001 | Kaye et al. ................... 250/575 |
| 6,239,710 | B1 | | 5/2001 | Oppelt |
| 6,519,033 | B1 | * | 2/2003 | Quist et al. .................. 356/337 |
| 6,606,157 | B1 | * | 8/2003 | Kaye et al. ................... 356/336 |
| 7,990,525 | B2 | * | 8/2011 | Kanda ............................ 356/73 |
| 8,711,353 | B2 | * | 4/2014 | Kaye et al. ................... 356/342 |
| 2003/0223063 | A1 | | 12/2003 | Hill et al. |
| 2005/0225745 | A1 | * | 10/2005 | Nagai ............................. 356/73 |
| 2007/0010974 | A1 | * | 1/2007 | Nicoli et al. ................. 702/196 |

OTHER PUBLICATIONS

European Patent Office, International Search Report and Written Opinion of the International Searching Authority, International Application No. PCT/GB2011/052028, dated Dec. 30, 2011 (18 pages).

* cited by examiner

SECOND GENERATION LOW-COST PARTICLE COUNTER

FIELD OF THE INVENTION

The present invention relates to a low cost apparatus and method for the detection of a fluid-borne particle. It is particularly applicable for the detection of a fluid-borne particle in an optically defined sensing zone.

BACKGROUND OF THE INVENTION

In many fields of environmental monitoring, workplace monitoring, pollution control, and occupational health monitoring, it is necessary to continuously measure the aerosol content of a local environment. Where real-time high-sensitivity measurements are desired, instruments are used that are capable of measuring the sizes of individual particles at high rates (typically thousands of particles per second) so that an accurate assessment of both the concentration of particles and their size distribution can be achieved.

The instruments that are commonly used for this purpose are 'optical particle counters' (OPC). These use an intense light source (usually a laser) to illuminate a narrow column of sample air drawn through a sensing chamber by an electrical air-pump. The air column is sufficiently narrow that the volume of air illuminated by the laser beam—often referred to as the particle 'sensing zone'—rarely contains more than a single particle, and the pulse of light scattered by this particle as it crosses the laser beam is recorded as a particle count, the magnitude of the pulse being indicative of the particle size according to a calibration function. The calibration function depends on factors such as the laser wavelength and beam power and the solid angular range over which the scattered light from the particle is recorded.

There are many excellent commercial varieties of OPC manufactured by companies such as Met One Instruments (USA), Grimm Aerosol Technik GmbH (Germany), and Casella Measurement Ltd., (UK). In all these instruments, the air-pump provides the necessary suction to draw the ambient air through a narrow sample tube and deliver the resulting column of air through the laser beam. The pump itself must be powerful enough to generate the required pressure drop inside the sensing chamber to draw the external air in through the sample tube. Furthermore, since the pumps are normally required to be protected from particulate contamination in the air, they are generally preceded in the air-flow by a high efficiency particle filter and this too will present a flow impedance which the pump must overcome. These features of conventional OPC's result in several drawbacks; firstly, the pumps used must overcome the pressure drops in the sample tube and particle filter, and this has implications for pump size and current consumption (and, by extension, for battery-life in standalone of hand-held units); secondly, the particle filters need to be periodically replaced (incurring further cost to user); and thirdly, the air sample handling system comprising sample inlet tube, vent tube, interconnecting tubing and filter, etc.), can be relatively complex to manufacture and assemble, with implications for final unit cost.

WO2008140816 (UNGER) describes a compact low cost particle sensor wherein the flow of fluid is directed to a detection zone via a series of baffles. The detection zone is basically a detector located directly under the laser beam which collects radiation scattered by particles passing through the beam. A problem with this device is that the detector is not able to distinguish the number or size of particles passing through the, rather large, detection zone. This device is only able to detect that at least one particle has passed through the detection zone, and in this regard it is little more than a portable smoke detector. This device cannot be used to accurately count the number of particles passing through the detection zone There is a need for an apparatus and method of aerosol monitoring, having single particle sensitivity, which requires no air-pump or particle filter, and which is mechanically very simple, thus offering the prospect of manufacture using a small number of parts.

GB 0917444.2 (University of Hertfordshire) describes one type of apparatus for the detection of a fluid-borne particle in an optically defined sensing zone wherein a first reflector or refractor means is adapted to direct radiation scattered from the fluid borne particle passing through the beam of radiation in the optically defined sensing zone into the first detector means and wherein the second reflector or refractor means is adapted to direct radiation scattered from the fluid borne particle passing through the beam of radiation in the optically defined sensing zone in to the second detector means.

SUMMARY OF THE INVENTION

According to a first aspect of the present invention there is provided an apparatus for the detection of a fluid-borne particle in an optically defined particle sensing zone, the apparatus comprising:
  i) a scattering chamber;
  ii) a means for providing a sample of fluid, containing the fluid-borne particle, in the form of a flow through the optically defined particle sensing zone;
  iii) a means for generating a beam of radiation through the optically defined particle sensing zone;
  iv) a single reflector or refractor means having a primary focus within the optically defined particle sensing zone and a secondary focus located outside the beam of radiation;
  v) a detector means comprising a first photosensitive detection area and a second photosensitive detection area;
  vi) a means for deriving data from the radiation detected by the first photosensitive detection area and second photosensitive detection area of the detection means
wherein the single reflector or refractor means is adapted to direct radiation scattered from the fluid borne particle passing through the beam of radiation within the optically defined particle sensing zone to the detection means located at the secondary focus of the single reflector or refractor means.

Single means only one.

Preferably the detector means comprises a single detector means wherein the first photosensitive detection area and the second photosensitive detection area are integral. The detector can be 'integral' in that both photosensitive areas are on the same piece of silicon, but they must still be electrically separate from one another. In this way the detectors are like a single 'chip' but fabricated to have the required inner and outer photosensitive areas which are electrically separate.

Alternatively the detector means comprises two detector means wherein the first detector means comprises the first photosensitive detection area and the second detector means comprises the second photosensitive detection area. In this alternative the two detector areas are discrete 'chips', ie: one with a hole in the middle into which the second detector fits.

Preferably the first photosensitive detection area is located wholly inside the second photosensitive detection area.

Preferably the second photosensitive detection area wholly surrounds the first photosensitive detection area.

Preferably the first photosensitive detection area is in the shape of a rectangle. The length (or width) of the rectangle governs the length of the laser beam (measured along the beam axis) that a particle can be detected in to the left or right to the primary focus of the single reflector or refractor. The centre of the length (or width) of the rectangle is coincident with the secondary focus of the single reflector or refractor means where light scattered from a particle at the primary focus of the single reflector or refractor means is reflected or refracted to. The height of the rectangle corresponds to be slightly larger than the path traced out by a particle as it passes through the laser beam at the primary focus of the single reflector or refractor means (i.e. the height of the rectangle is slightly greater than the thickness of the laser beam along its minor axis for a laser beam with an elliptical cross section, the difference being a result of the magnification of the optical system, namely the distance from the detector to the reflector or refractor surface divided by the distance of the particle to the reflector or refractor surface).

Preferably the second photosensitive detection area is in the shape of a circle

Preferably the optically defined sensing zone comprises a first zone and a second zone wherein the second zone is smaller than the first zone and wherein the second zone is located wholly inside the first zone. The first zone of the optically defined sensing zone corresponds to the cross-sectional area of the laser beam orthogonal to the fluid flow direction within which a particle will scatter light to the single reflector or refractor with this light subsequently being reflected or refracted by the single reflector or refractor means to the first photosensitive detection area of the detector means. The second zone of the optically defined sensing zone corresponds to the cross-sectional area of the laser beam orthogonal to the fluid flow immediately outside the first zone within which a particle will scatter light to the single reflector or refractor with this light subsequently being reflected or refracted by the single reflector or refractor means to the second photosensitive detection area of the detector means.

Preferably the single reflector or refractor means is adapted to direct radiation scattered from the fluid borne particle passing through the beam of radiation within the first zone of the optically defined sensing zone to the first photosensitive detection area of the detection means.

Preferably the single reflector or refractor means is adapted to direct radiation scattered from the fluid borne particle passing through the beam of radiation within the second zone of the optically defined sensing zone to the second photosensitive detection area of the detection means.

Preferably the means for deriving data from the radiation detected by the first photosensitive detection area and second photosensitive detection area of the detection means is adapted such that only particles passing through the first zone of the optically defined sensing zone are counted and/or sized.

Preferably the means for deriving data from the radiation detected by the first photosensitive detection area and second photosensitive detection area of the detection means is adapted such that particles detected only by the first photosensitive detection area are counted and/or sized.

Preferably the means for deriving data from the radiation detected by the first photosensitive detection area and second photosensitive detection area of the detection means is adapted such that particles detected by both the first photosensitive detection area and at a predetermined intensity by the second photosensitive detection area are counted and/or sized.

Preferably the criterion for counting a particle and thus the predetermined intensity as stated above is calculated by comparing the intensity of radiation from the particle detected in the first photosensitive detection area and the intensity of radiation detected from the particle in the second photosensitive detection area and wherein when the intensity of radiation detected in the second photosensitive detection area is equal to or less than 25% of the intensity radiation detected in the first photosensitive detection area then the measurement is deemed 'valid' and the particle is counted and/or sized. More preferably when the intensity of radiation detected in the second photosensitive detection area is equal to or less than 20% of the intensity radiation detected in the first photosensitive detection area the particle is counted and/or sized, still more preferably when the intensity of radiation detected in the second photosensitive detection area is equal to or less than 15% of the intensity radiation detected in the first photosensitive detection area the particle is counted and/or sized, yet more preferably when the intensity of radiation detected in the second photosensitive detection area is equal to or less than 10% of the intensity radiation detected in the first photosensitive detection area the particle is counted and/or sized, even more preferably when the intensity of radiation detected in the second photosensitive detection area is equal to or less than 5% of the intensity radiation detected in the first photosensitive detection area the particle is counted and/or sized. In each case, the sizing of the particle is typically achieved by comparing the magnitude of the electrical signal from the first photosensitive detection area to a calibration function based on the light scattering of particles of know sizes.

As this detector assembly requires only a single reflector or refractor means and a single detector means this may have the effect of providing a low cost apparatus for counting and sizing particles which operates by providing an optically defined rather than physically defined (by for example, a narrow fluid delivery tube) particle sensing zone in which particles are detected. The dual optical sensing zone allows not only for particles to be detected but also to be counted and sized accurately. In situations where there is an existing airflow (eg: the apparatus is attached to a moving vehicle or aircraft or is moved by hand through the air) in a direction relative to the broad axis of the elliptical cross-section laser beam, the apparatus is able to operated without the need of a pump to draw a sample through a narrow chamber, as in conventional optical particle counters. Given that there is no pump and that the apparatus parts are simple, light and cheap to construct, this apparatus provides a low cost hand held device with single particle sensitivity. Furthermore, as this detector assembly requires only a single reflector or refractor means and a single detector means this may have the further effect of allowing the single reflector or refractor means and single detector means combination to be placed at any angle in the plane containing the broad axis of the laser beam, providing the mirror or detector do not obstruct the beam of radiation.

Preferably the apparatus further comprises focussing means adapted to focus the beam of radiation such that the beam of radiation has an elliptical cross-section. More preferably the major axis of the elliptical cross-section is orthogonal to the direction of fluid flow.

Preferably the beam of radiation is generated using a diode laser.

Preferably the means for providing a sample of fluid in the form of a flow through the optically defined sensing zone comprises an open ended chamber, referred to as a scattering chamber, of a diameter large compared to the optically defined sensing zone which is typically located at or close to the centre of the chamber through which fluid can freely flow. By selecting a scattering chamber diameter which is larger than the diameter of the optical sensing zone, the air, or other fluid sample, can freely flow through the scattering chamber. There is therefore no need for the air, or other fluid sample, to be sucked through the scattering chamber as in prior art devices, but whilst still retaining the desired single particle sensitivity without a pump.

In cases where there is no natural air or fluid flow in the environment, the means for providing a sample of fluid in the form of a flow through the optically defined sensing zone preferably comprises a fan. This may have the effect that a flow of air can be provided cheaply and with low weight and low power usage to help draw air, or other fluid sample through the apparatus. Alternatively the apparatus could be "waved" (i.e. moved through the air, for example manually by the user or attached to a moving vehicle) through the air to generate a flow of air or other fluid. Alternatively the apparatus can be placed in an environment wherein the fluid sample will flow through the optically defined sensing zone, such as an environment of sample air moving relative to the apparatus by convection or within an air-conditioning duct.

Preferably the single reflector or refractor means comprises a mirror. More preferably the mirror comprises a concave mirror. Still more preferably the concave mirror comprises an elliptical concave mirror. This allows the mirror to be used to not only to reflect the scattered radiation towards the single detector means, but also to focus the radiation so that a greater sample of scattered radiation is detected from the particle.

Preferably the single reflector means is integrally formed in the scattering chamber. This is advantageous as there are fewer parts to produce and producing fewer parts is cheaper resulting in a lower cost apparatus.

Preferably the scattering chamber is formed from an injection moulded plastics material. This is advantageous as injection moulding of plastics is a cheap process to run to mass produce identical items, resulting in a lower cost apparatus.

Preferably a single concave surface is formed integrally within the scattering chamber. Still more preferably a single concave elliptical surface is formed integrally within the scattering chamber.

Preferably the single concave surface is provided with a reflective material to form the single reflector or refractor means. This is advantageous as the mirror is formed internally to the scattering chamber, in the correct position, in a single step and coated with a reflective material. This results in a lower cost apparatus due to reduced parts and also because the mirrors are automatically positioned correctly.

According to a second aspect of the present invention there is provided a method for the detection of a fluid-borne particle in an optically defined particle sensing zone, the method comprising:
 i) providing a sample of fluid, containing the fluid-borne particle, in the form of a flow through the optically defined sensing zone;
 ii) directing a beam of radiation that illuminates the optically defined sensing zone and with uniform intensity of radiation;
 iii) detecting radiation scattered by the fluid-borne particle as it passes through the beam of radiation in the optically defined sensing zone.

Preferably the method employs an apparatus for the detection of a fluid-borne particle in an optically defined particle sensing zone, the apparatus comprising:
 i) a scattering chamber;
 ii) a means for providing a sample of fluid, containing the fluid-borne particle, in the form of a flow through the optically defined particle sensing zone;
 iii) a means for generating a beam of radiation through the optically defined particle sensing zone;
 iv) a single reflector or refractor means having a primary focus within the optically defined particle sensing zone and a secondary focus located outside the beam of radiation;
 v) a single detector means comprising a first photosensitive detection area and a second photosensitive detection area;
 vi) a means for deriving data from the radiation detected by the first photosensitive detection area and second photosensitive detection area of the detection means wherein the single reflector or refractor means is adapted to direct radiation scattered from the fluid borne particle passing through the beam of radiation within the optically defined particle sensing zone to the detection means located at the secondary focus of the single reflector or refractor means.

According to a third aspect of the present invention there is provided a method for the detection of a fluid-borne particle in an optically defined particle sensing zone, the method comprising:
 i) providing an apparatus having; a scattering chamber, a means for generating a beam of radiation, a single reflector or refractor means, a single detector means comprising a first photosensitive detection area and a second photosensitive detection area;
 ii) providing a sample of fluid in the form of a flow through the optically defined particle sensing zone;
 iii) directing the beam of radiation to illuminate the optically defined particle sensing zone with uniform intensity of radiation; and
 iv) deriving data from the radiation detected by the first photosensitive detection area and second photosensitive detection area of the detection means;

wherein the single reflector or refractor means is adapted to direct radiation scattered from the fluid borne particle passing through the beam of radiation within the optically defined particle sensing zone to the detection means located at the secondary focus of the single reflector or refractor means.

According to a fourth aspect of the present invention there is provided a method for the detection of a fluid-borne particle in an optically defined particle sensing zone, the method comprising:
 i) providing an apparatus according to the first aspect of the present invention;
 ii) providing a sample of fluid in the form of a flow through the optically defined particle sensing zone;
 iii) directing a beam of radiation that illuminates the optically defined particle sensing zone with uniform intensity of radiation; and
 iv) deriving data from the radiation detected by the first photosensitive detection area and second photosensitive detection area of the detection means.

The present invention seeks to provide a method of aerosol monitoring (having single particle sensitivity) which requires no air-pump or particle filter, and which is mechanically very simple, thus offering the prospect of manufacture using a small number of injection-moulded plastic parts. The air-movement may be achieved using a small electrical fan (far lower current consumption than a rotary-vane or diaphragm air-pump), by exploiting the natural movement of the ambient air (e.g.: wind, convection flow, etc.), or by simply moving the sensor unit itself through the air by hand or by attaching to a moving vehicle (car, train, aircraft, etc).

The present invention is based on the principle of optically defining a particle sensing zone rather than mechanically defining the zone as in conventional OPCs. As mentioned above, OPCs typically use a narrow airflow delivery tube to confine the sample airflow to a narrow column, typically ~1 mm in diameter, which is directed through a narrow ribbon-shaped laser beam such that the intersection between the beam and the airflow—the sensing zone—is sufficiently small that it very rarely contains more than a single particle even when measuring high-concentration aerosols. Avoiding 'particle coincidences' where two or more particles occupy the sensing zone at any instant is crucial to obtaining unbiased aerosol size and concentration data.

In the present Invention, the sample air does not pass through a narrow delivery tube as in conventional OPCs, but instead passes through a far wider chamber that may or may not have cylindrical tube-like geometry. The particles carried by the air moving though this chamber are not constrained to move in single file by any mechanical tube or other device. The single-particle sensing zone is instead defined by suitable optical components.

BRIEF DESCRIPTION OF THE DRAWINGS

A preferred embodiment of the present invention will now be more particularly described, by way of example only, with reference to the accompanying drawings, wherein.

DESCRIPTION OF THE PREFERRED EMBODIMENTS

Figure 1:
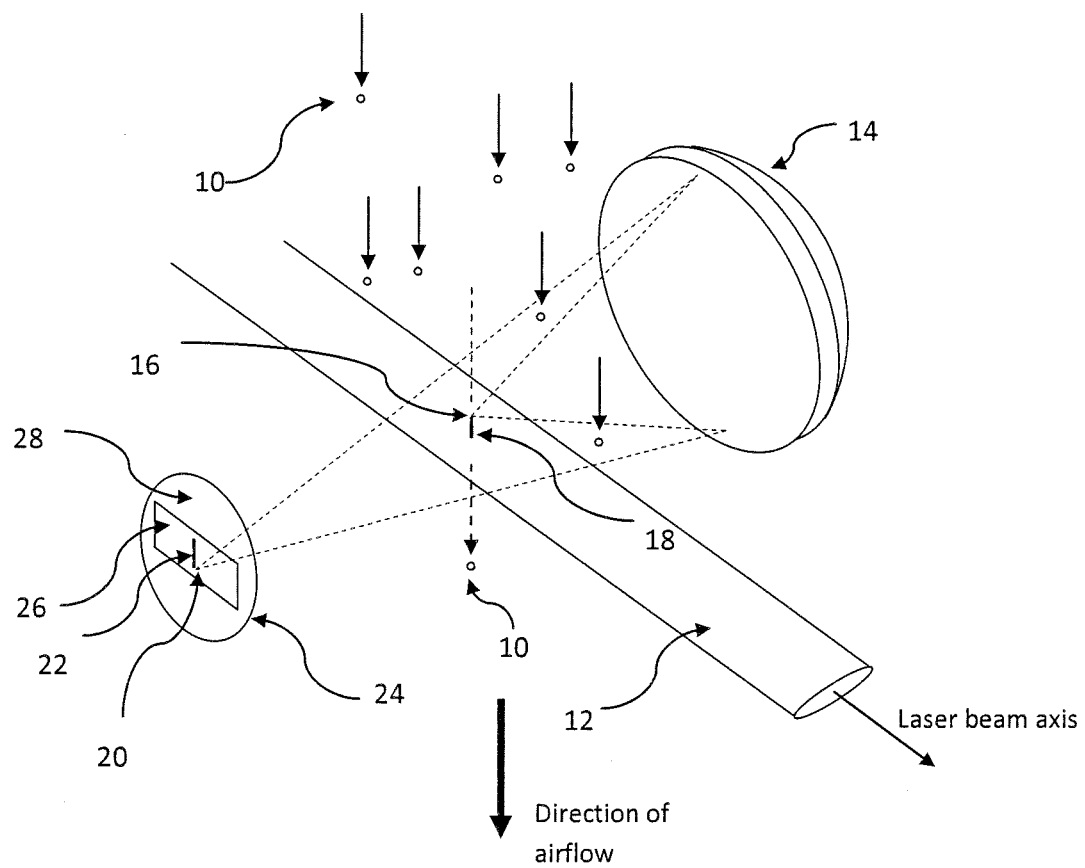
FIG. 1 shows a perspective view of the particle detection apparatus according to a first embodiment of the present invention.

The preferred embodiment requires a flow of particles 10 carried in a moving airstream to pass through a laser beam 12, where the axis of the laser beam is orthogonal to the direction of the airflow, as in FIG. 1. The particles 10 are not constrained and may pass anywhere through the laser beam 12. It is well known that the size of a particle may be determined by measuring at some angle the intensity of light scattered by the particle as it passes through the beam. However, the non-uniform intensity profile of the beam (typically Gaussian) means that a particle passing through the edge of the beam will be illuminated with a lower intensity of light than an identically-sized particle passing through the centre of the beam. It will thus scatter less light and will be measured as smaller than the particle passing through the centre of the beam.

Because of this potential source of particles sizing error, it is necessary to optically define a small sensing zone within the central part of laser beam where the intensity variation is small, so that only particles passing through this zone will be 'seen' by the detection system. Thus, all particles will experience essentially the same intensity of illuminating light and will therefore be accurately sized.

The preferred embodiment for achieving this optical sensing zone is shown in FIG. 1. The laser beam 12 is focused through a cylindrical lens (not shown) such that it forms a flat, elliptical cross-section, with the major axis of the ellipse being orthogonal to the direction of the airflow carrying the particles 10. Positioned approximately in the same horizontal plane as the major axis of the flattened laser beam is reflector or refractor means, which in the present embodiment is an elliptical mirror 14. The mirror is positioned such that its primary focus 16 lies on the axis of the laser beam 12. The angle of the mirror axis to the laser beam 12 axis may be typically about 90 degrees (both being essentially perpendicular to the direction of the fluid flow), although the mirror could be at other angles to the beam without detriment to the performance of the apparatus. An elliptical mirror is preferred to a spherical mirror as an elliptical mirror tends to suffer lower optical aberrations, and it is important to have low optical aberrations in this present embodiment. However it is not essential that the mirror is elliptical and in an alternative a spherical mirror can be employed. In a further alternative a spherical or elliptical lens may be employed.

Consider a particle 10 that passes through the laser beam 12 exactly coincident with the primary focus 16 of the elliptical mirror 14. As it passes through the laser beam 12, the particle 10 will trace out a short vertical path 18 orthogonal to the laser beam 12 axis as shown in FIG. 1, and will scatter light in all directions whilst travelling along this path. Some of this light will fall onto the elliptical mirror 14 and will be reflected to the secondary focus 20 of the elliptical mirror 14. The trajectory of the particle 10 through the laser beam 12 therefore results in a thin vertical line of light 22 (a "pencil line") at the secondary focus 20 of the elliptical mirror 14, as shown in FIG. 1.

Positioned at this secondary focus 20 and facing the mirror 14 is a detection means, which is typically a photodetector 24. The photodetector 24, typically a photodiode, comprises two separate photosensitive areas, a first photosensitive area being an inner rectangular area 26 surrounded by a second photosensitive area being an outer area 28 (typically, but not essentially, circular). The first photosensitive area 26 is of a height just slightly larger than the length of the pencil line of light 22 scattered by the particle 10 as it passes through the laser beam 12. The photodetector 24 is positioned such that this line of light 22 exactly bisects the rectangular photosensitive area 26, as shown in FIG. 1. As described below, the width of the rectangular photosensitive area 26 determines the size of the optical sensing zone centred upon the primary focus 16 of the elliptical mirror 14 in the laser beam 12.

Figure 2:
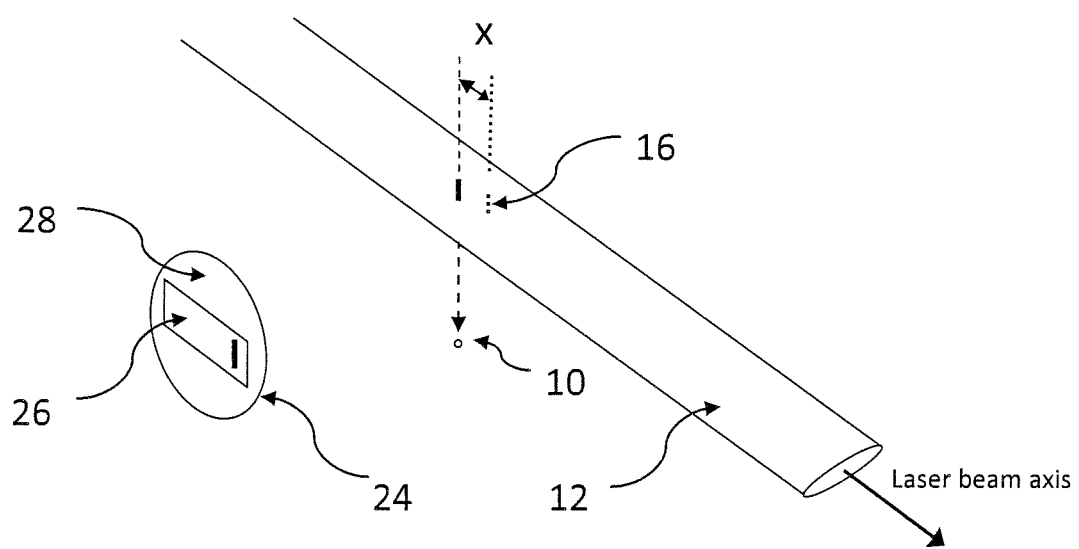
FIG. 2 shows a perspective view of the first and second photosensitive areas of the light detector means of the particle detection apparatus of FIG. 1 for a particle traversing the beam a distance x upstream from the primary focal point of the reflector or refractor means.

FIGS. 2 to 5 illustrate the behaviour of this optical system for various particle trajectories through the laser beam. For clarity, only the laser beam 12 and the photodetector 24 are shown. Consider in FIG. 2 a particle 10 passing through the laser beam 12 a very short distance 'x' upstream along the laser beam axis from the primary focus 16 of the elliptical mirror (to the left of the primary focus in FIG. 2). The scattered line of light reflected from the mirror will fall onto the inner photosensitive area 26 of the photodiode detector but to the right of the centre-line of that area, as shown in FIG. 2.

It follows that if another particle was to subsequently pass through the laser beam slightly further upstream along the laser beam axis from the primary focus 16 of the elliptical mirror than the particle described above, the line of scattered light it produced on the photodiode 24 may be just beyond the end of the rectangular photosensitive area 26, instead falling onto the outer photosensitive area 28. Similarly, another particle passing through the laser beam 12 at a distance downstream along the laser beam axis from the elliptical mirror 14 primary focus 16 (to the right of the primary focus in FIG. 2) will result in a line of scattered light falling on the rectangular photosensitive area 26 but in the left half of that detector area.

By this example, it can be seen that the width of the rectangular photosensitive area 26 effectively defines the length of the laser beam 12 through which particles can traverse and be detected by the rectangular photosensitive area 26. Particles traversing the laser beam slightly further upstream or downstream along the laser beam axis will instead result in light falling onto the outer photosensitive area 28. Particles passing through the laser beam even further upstream or downstream from the primary focus of the mirror will result in scattered light that passes beyond the edge of the outer photosensitive area 28 and is therefore not detected at all.

Figure 3:
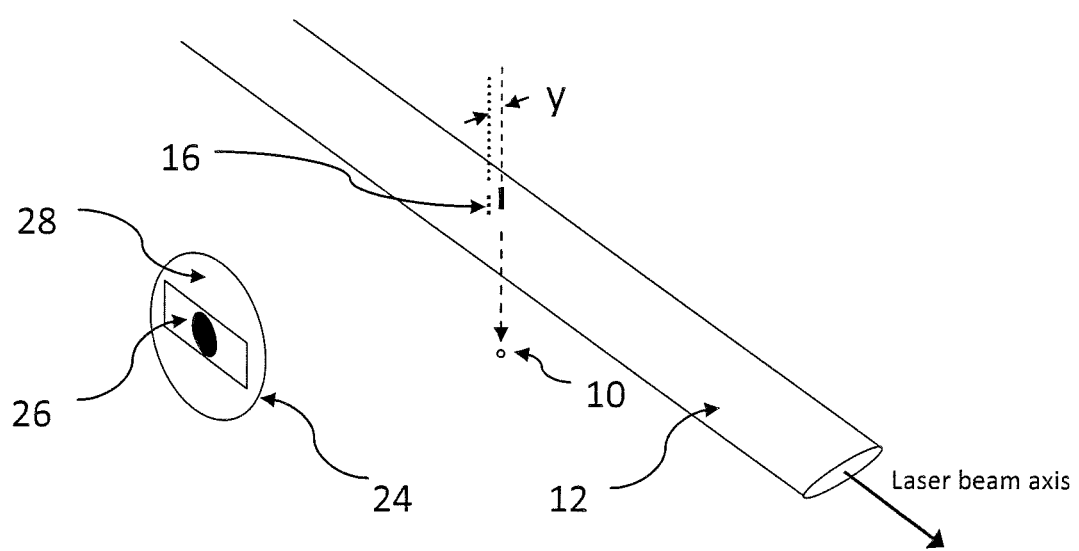
FIG. 3 shows a perspective view of the first and second photosensitive areas of the light detector means of the particle detection apparatus of FIG. 1 with a particle traversing the beam a distance y closer to reflector or refractor means than the primary focal point of the reflector or refractor means but still such that the light scattered by the particle falls entirely within the first photosensitive area of the detector means.

In a similar way, a particle that traverses the laser beam a lateral distance 'y' from the primary focus 16 of the elliptical mirror 14 (ie a distance y along the major axis of the beam's elliptical cross-section from the centre line of the laser beam, parallel with its longitudinal axis), as shown in FIG. 3, will result in a pattern of scattered light on the photodetector 24 that is not a sharp pencil-line of light but rather, because it is out of focus, an approximately circular patch of light. Because the height of the rectangular photosensitive area is slightly greater than the normal height of the pencil-line of light (scattered by a particle passing through the exact primary mirror focus), it will still be all captured by the photosensitive area provided the lateral displacement 'y' of the particle trajectory is small.

Figure 4:
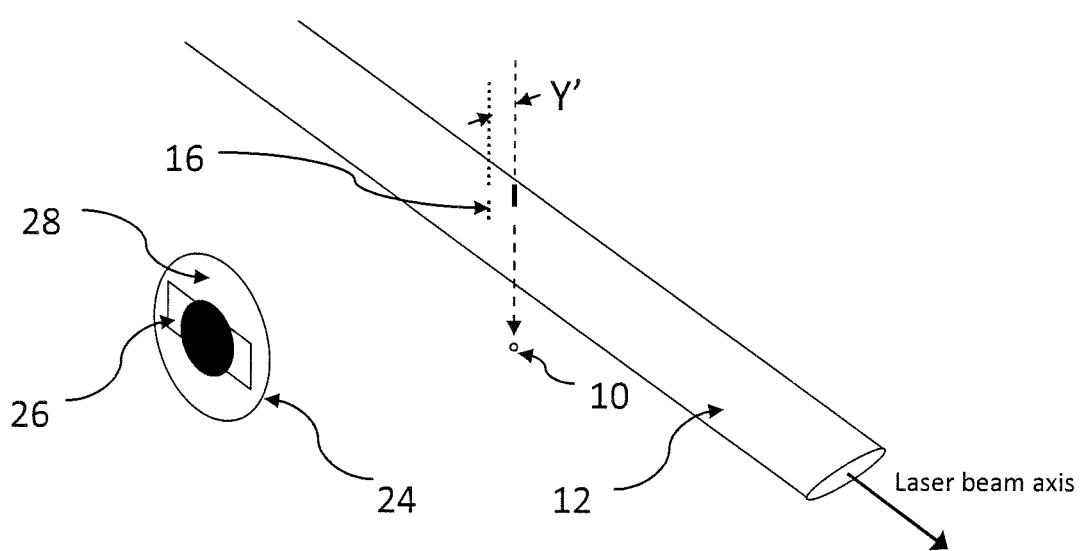
FIG. 4 shows a perspective view of the first and second photosensitive areas of the light detector means of the particle detection apparatus of FIG. 1 with a particle traversing the laser beam a distance y' (where y' is greater than y in FIG. 3) closer to reflector or refractor means than the primary focal point of the reflector or refractor means such that the light scattered by the particle no longer falls entirely within the first photosensitive area of the detector means.

However, if the lateral displacement of the particle trajectory from the mirror focus 16 is increased to y', the patch of scattered light will begin to extend above and below the rectangular photosensitive area 26 of the photodetector, as in FIG. 4. The further the particle trajectory is to the side of the axis of the laser, the higher the fraction of the scattered light that will therefore fall onto the outer photosensitive area 28 of the photodetector 24. The same thing happens if the particle trajectory is displaced laterally to the opposite side of the primary focus of the mirror 16.

Figure 5:
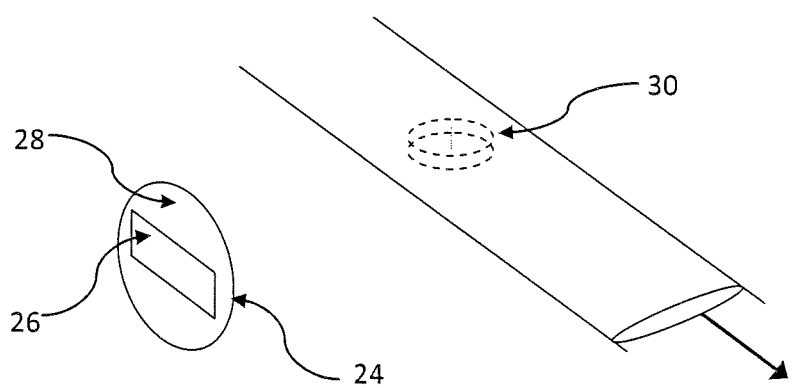
FIG. 5 shows a perspective view of the first and second photosensitive areas of the detector means of the particle detection apparatus of FIG. 1 indicating the extent of the first zone of the optically defined particle sensing zone within the laser beam.

The net result is that the size of the rectangular photosensitive area 26 effectively defines an optical 'sensing zone' 30 within the laser beam, as in FIG. 5. All particles passing through this zone will scatter light that is wholly captured by the rectangular sensing area 26 of the photodiode 24, with none falling into the outer photosensitive area 28. The electrical output from area 26 may therefore be used to not only register (count) the particle, but also, since the beam intensity is designed to be uniform across the sensing zone 30, from the magnitude of the electrical signal, it can be used to estimate the particle size. Particles passing through the edge of this sensing zone 30 will scatter some light to the outer photosensitive area 28 of the photodiode 24 and if the output of this photosensitive area 28 reaches a pre-set fraction (say, 25%) of the coincident output falling onto the inner photosensitive area 26, the particle will be deemed to have crossed outside of the sensing zone 30 and will not be recorded.

The elliptical mirror 14 and photodetector 24, therefore provide an effective and efficient (in terms of fewest component parts required) method of optically defining a sensing zone within the illuminating laser beam. Such an arrangement will allow the accurate estimation of both the particle size distribution and, since the cross-sectional area of the sensing zone can be accurately determined, also the concentration of particles carried in the air flowing through the laser beam. No mechanical tubing or similar device to constrain the trajectories of the particles is required, and consequently nor is any mechanical air-pump required to draw air through such tubing. This represents a saving of cost and electrical power requirements in the measurement of airborne particles. Indeed, if the particles to be measured are carried in a natural airflow (wind or draught), the apparatus described herein would be capable of achieving this measurement without the need for any moving parts, with the benefit of enhanced lifetime and reliability over conventional 'pumped-air' particle measurement devices.

Figure 6:
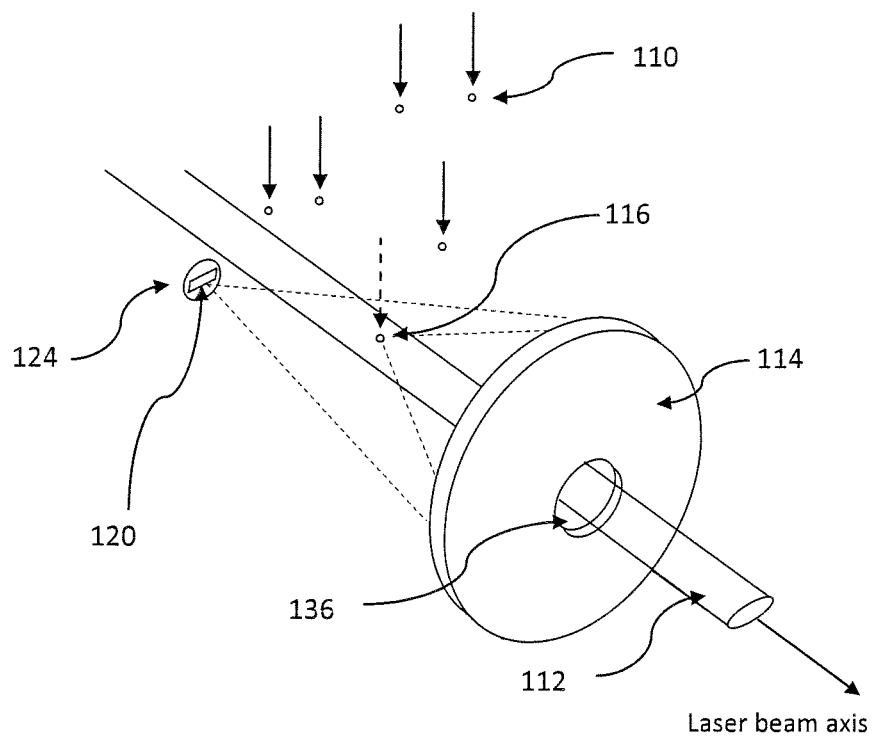
FIG. 6 shows a perspective view of the particle detection apparatus according to a second embodiment of the present invention wherein the laser beam passes through a hole provided in the reflector or refractor means.

FIG. 6 illustrates an alternative embodiment of the present invention wherein the elliptical mirror 114 is provided with a small hole 136 at its centre sufficient to allow the laser beam 112 to pass through unaffected whilst still ensuring the primary focus 116 of the mirror 114 lies on the laser beam 112 axis. The above measurement methodology would still apply. It would simply require the mirror 114 to be slightly tilted so that the secondary focus 120 of the mirror 114 fell to the side of the laser beam 112 (ie: the photodetector 124 would not obstruct the laser beam 112). Such a configuration could be advantageous in areas where space requirements of the apparatus need to be minimised.

Figure 7:
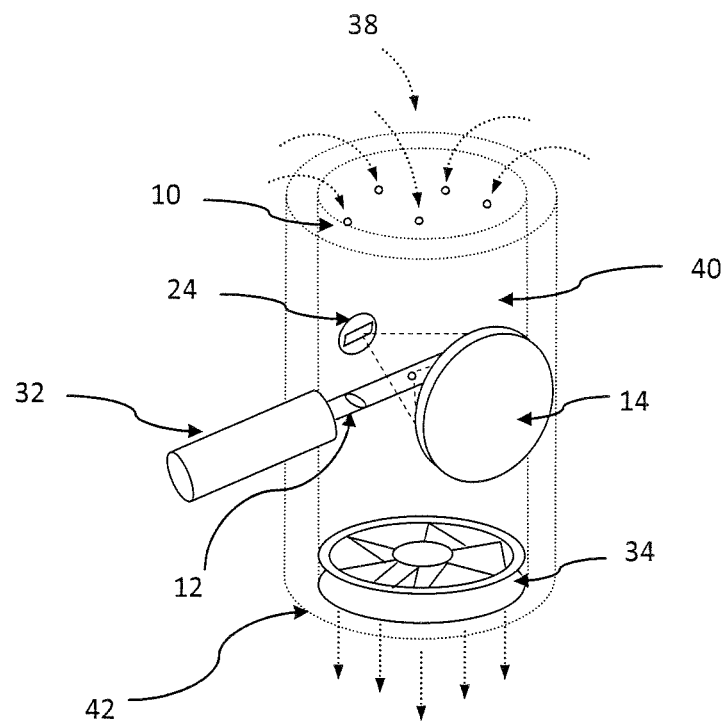
FIG. 7 shows a cross-sectional view of the scattering chamber which houses the particle detection apparatus of FIG. 1 according to a third embodiment.
Figure 8:
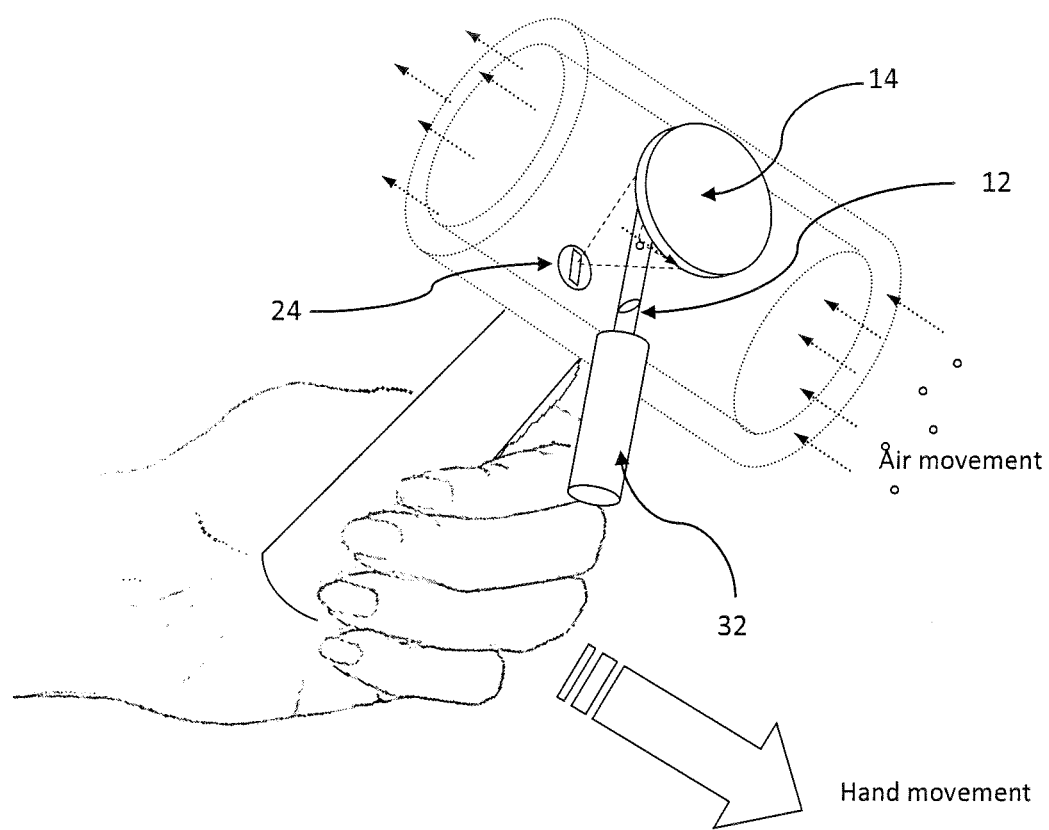
FIG. 8 shows a cross-sectional view of the scattering chamber which houses the particle detection apparatus of FIG. 1 according to a fourth embodiment.

FIG. 7 illustrates a cross-sectional view of the particle detector 42 which houses the particle detection apparatus of FIG. 1 according to a third embodiment. In this embodiment, a small low-power electrical fan 34 causes particle-laden ambient air 38 to move through a scattering chamber 40 at a desired rate. The fan 34, in one alternative, is of a type commonly used to cool computer microprocessors, requiring a current of only a few milliamps; far less than the tens-of-milliamp currents required by conventional OPC air-pumps. The scattering chamber 40 has end-caps (not shown) that do not restrict the airflow but act as light baffles to prevent entry of ambient daylight or room-light. An alternative arrangement can be seen in FIG. 8. The FIG. 8 embodiment does not have a fan, but instead is adapted to be manually waved through the air by a user.

Typically, for normal ground level applications, the particles being detected by the apparatus would be in the important respirable size range of around 0.5 to 15 μm in diameter.

The concentration of particles may be computed using the product of the air velocity through the sensing zone and the cross-sectional area of sensing zone. This velocity may be determined from a knowledge of the laser beam-depth, being the minor axis of its elliptical beam cross-section, and the time-of-flight of the particle through the beam, as measured from the duration of the electrical signal from detector. Typically for normal ground level applications the minor axis of the elliptical cross-section of the beam of radiation is around 100 μm and the major axis is around 2 mm.

The maximum measurable particulate concentration will be reached when the probability of more than one particle being within the sensing zone reaches an unacceptable level, typically ~2%. The beam depth and sensing zone cross-section are selected such that this would not occur for concentrations less than typically a thousand particles per milliliter of air.

The apparatus as described offers several advantages over conventional OPCs;

Mechanical simplicity. The absence of internal pipework, filters, and tubing common in conventional OPC units means that the invention could be fabricated at a low manufacturing cost, especially if specialist plastic injection moulded parts (including mirrored surfaces) were employed. In such a case, the scattering chamber comprises two semi-cylindrical parts, the first part with integral an integral elliptical mirrored surface and the second part with the detection means. The integral mirrored surface would be formed by injection moulding the scattering chamber with an integral concave surface which would then be provided with a coating of a reflective material.

An air fan (if provided) would be capable of moving large volumes of air, required in efficient ambient monitoring, with very low power consumption, since it would be operating against minimal pressure drop. This could significantly extend the battery life of a standalone or hand-held unit compared to that in a conventional OPC with comparable sample air flow-rate. Indeed, the fan would not be necessary at all in some cases. For example, where the airflow through the sensor unit was generated by movement of the unit itself through the air, such as 'waving' a hand-held unit at arm's length. Such a 'no moving parts' implementation of the invention would be not only be even cheaper to manufacture than the fan-assisted version of the invention but would also offer improved reliability, it having no moving parts to wear out.

In addition as no pump is required, the scattering chamber does not need to be air-tight. In conventional OPC devices where a pump is required to suck the air through the narrow mechanically defined sensing zone, the scattering chamber needs to be air-tight because of the air pressure differential required to cause the air to flow through the narrow mechanically defined sensing zone is significant. In the present invention there is virtually no air pressure differential needed as the scattering chamber is large and open-ended and the sensing zone is defined optically rather than mechanically. So air-tightness of the scattering chamber is unnecessary. This means that the scattering chamber can be formed from low dimensional tolerance plastic components rather than the high precision (usually metal) components needed for an air-tight chamber. This allows for a cheaper and lighter apparatus to be constructed.

Further in addition, if a fan is employed the fan is located below the sensing zone such that any particles depositing on the fan blades have already been detected.

The apparatus would require no periodic replacement of internal filter units, making it more suitable than conventional OPCs in remote or hostile monitoring environments where manual filter replacement is undesirable on grounds of inaccessibility or safety hazard.

The invention claimed is:

1. An apparatus for the detection of a fluid-borne particle in an optically defined particle sensing zone, the apparatus comprising:
   i) a scattering chamber configured to receive
      a sample of fluid, containing the fluid-borne particle, in the form of a flow through the optically defined particle sensing zone;
   ii) a diode laser for generating a beam of radiation through the optically defined particle sensing zone;
   iii) a single reflector or refractor having a primary focus within the optically defined particle sensing zone and a secondary focus located outside the beam of radiation; and
   iv) a single scattered light detector comprising a first photosensitive detection area and a second photosensitive detection area, wherein the first photosensitive detection area and the second photosensitive detection area are integral and the first photosensitive detection area is located wholly within the second photosensitive detection area, and wherein the scattered light detector is configured to generate
   electrical signals representative of the radiation detected by the first photosensitive detection area and second photosensitive detection area,
   wherein the single reflector or refractor is adapted to direct radiation scattered from the fluid borne particle passing through the beam of radiation within the optically defined particle sensing zone to the scattered light detector located at a secondary focus of the single reflector or refractor, wherein the optically defined sensing zone compromises a first zone defined by radiation detected by the first photosensitive detection area of the scattered light detector and a second zone defined by radiation detected by the second photosensitive detection area of the scattered light detector, wherein the first zone is smaller than the second zone, and wherein the first zone is located wholly inside the second zone.

2. An apparatus according to claim 1 wherein the first photosensitive detection area is in the shape of a rectangle 3. An apparatus according to claim 1 wherein the second photosensitive detection area is in the shape of a circle.

4. An apparatus according to claim 1 wherein the single reflector or refractor is adapted to direct radiation scattered from the fluid borne particle passing through the beam of radiation within the first zone of the optically defined sensing zone to the first photosensitive detection area of the scattered light detector.

5. An apparatus according to claim 1 wherein the single reflector or refractor is adapted to direct radiation scattered from the fluid borne particle passing through the beam of radiation within the second zone of the optically defined sensing zone to the second photosensitive detection area of the scattered light detector.

6. An apparatus according to claim 1 wherein the single scattered light detector is configured to generate the electrical signals such that particles detected only by the first photosensitive detection area are counted.

7. An apparatus according to claim 1 wherein the single scattered light detector is configured to generate the electrical signals such that particles detected by both the first photosensitive detection area and at a predetermined intensity by the second photosensitive detection area are counted.

8. An apparatus according to claim 7 wherein a predetermined intensity is calculated by comparing an intensity of radiation from the particle detected in the first photosensitive detection area and an intensity of radiation detected from the particle in the second photosensitive detection area and wherein when the intensity of radiation detected in the second photosensitive detection area is equal or less than 25% of the intensity radiation detected in the first photosensitive detection area the particle is counted.

9. An apparatus according to claim 1 wherein the single reflector or refractor comprises a mirror.

10. An apparatus according to claim 9 wherein the mirror comprises a concave mirror.

11. An apparatus according to claim 10 wherein the concave mirror comprises an elliptical concave mirror.

12. An apparatus according to claim 1 wherein the single reflector is integrally formed in the scattering chamber.

13. An apparatus according to claim 1 wherein the scattering chamber is formed from an injection moulded plastics material.

14. An apparatus according to claim 1 wherein a single concave surface is formed integrally within the scattering chamber.

15. An apparatus according to claim 14 wherein the single concave surface is a concave elliptical surface.

16. An apparatus according to claim 14 wherein the single concave surface is provided with a reflective material to form the single reflector or refractor.

17. A method for the detection of a fluid-borne particle in an optically defined particle sensing zone, the method comprising:
   i) providing an apparatus having a scattering chamber, a diode laser for generating a beam of radiation, a single reflector or refractor, a single scattered light detector comprising a first photosensitive detection area and a second photosensitive detection area;
   ii) providing a sample of fluid on the form of a flow through the optically defined particle sensing zone;
   iii) directing the beam of radiation to illuminate the optically defined particle sensing zone with uniform intensity of radiation; and
   iv) deriving data from the radiation detected by the first photosensitive detection area and second photosensitive detection area;
   wherein the single reflector or refractor is adapted to direct radiation scattered from the fluid borne particle passing through the beam of radiation within the optically defined particle sensing zone to the single scattered light detector located at a secondary focus of the single reflector or refractor means and wherein the optically defined sensing zone comprises a first zone and a second zone wherein the first zone is smaller than the second zone and wherein the first zone is located wholly inside the second zone.

18. A method for the detection of a fluid-borne particle in an optically defined particle sensing zone, the method comprising:
   i) providing a apparatus as claimed in claim 1;
   ii) providing a sample of fluid in the form of a flow through the optically defined particle sensing zone;
   iii) directing a beam of radiation that illuminates the optically defined particle sensing zone with uniform intensity of radiation; and
   iv) deriving data from the radiation detected by the first and second photosensitive detection areas of the single scattered light detector.

19. An apparatus according to claim 1 wherein the single scattered light detector is configured to generate the electrical signals such that particles detected only by the first photosensitive detection area are sized.

20. An apparatus according to claim 1 wherein the single scattered light detector is configured to generate the electrical signals such that particles detected only by the first photosensitive detection area are counted and sized.

21. An apparatus according to claim 1 wherein the single scattered light detector is configured to generate the electrical signals such that particles detected by both the first photosensitive detection area and at a predetermined intensity by the second photosensitive detection area are sized.

22. An apparatus according to claim 1 wherein the single scattered light detector is configured to generate the electrical signals such that particle detected by both the first photosensitive detection area and at a predetermined intensity by the second photosensitive detection area are counted and sized.

23. An apparatus according to claim 21 wherein a predetermined intensity is calculated by comparing an intensity of radiation detected from the particle in the first photosensitive detection area and an intensity of radiation detected from the particle in the second photosensitive detection area and wherein when the intensity of radiation detected in the second photosensitive detection are is equal to or less that 25% of the intensity radiation detected in the first photosensitive detection area the particle is sized.

24. An apparatus according to claim 22 wherein a predetermined intensity is calculated by comparing an intensity of radiation from the particle detected in the first photosensitive detection area and an intensity of radiation detected from the particle in the second photosensitive detection areas and wherein when the intensity of radiation detected in the second photosensitive detection area is equal to or less than 25% of the intensity radiation detected in the first photosensitive detection area the particle is counted and sized.

* * * * *

UNITED STATES PATENT AND TRADEMARK OFFICE
CERTIFICATE OF CORRECTION

| | | |
|---|---|---|
| PATENT NO. | : 9,116,121 B2 | Page 1 of 2 |
| APPLICATION NO. | : 13/881570 | |
| DATED | : August 25, 2015 | |
| INVENTOR(S) | : Paul Henry Kaye et al. | |

It is certified that error appears in the above-identified patent and that said Letters Patent is hereby corrected as shown below:

On the Title Page:

Item (73) Assignee:, change "UH Ventures Limited, Hartfield (GB)" to --UH Ventures Limited, Hatfield (GB)--.

Item (57) Abstract, line 12, change "a first photosensitive detection area (26) a second photosensitive detection area (29);" to --a first photosensitive detection area (26), a second photosensitive detection area (29);--.

In the Specification:

In column 1, line 54, change "in standalone of hand-held units);" to --in standalone or hand-held units);--.

In column 4, line 28, change "particles of know sizes." to --particles of known sizes.--.

In column 4, line 41, change "the apparatus is able to operated" to --the apparatus is able to be operated--.

In column 5, line 25, change "This allows the mirror to be used to not only to reflect the scattered radiation" to --This allows the mirror to be used not only to reflect the scattered radiation--.

In column 6, line 22, change "i) providing an apparatus having; a scattering chamber," to --i) providing an apparatus having a scattering chamber,--.

In column 9, line 38, change "(ie a distance y along" to --(i.e., a distance y along--.

In column 10, line 38, change "(ie: the photodetector 124" to --(i.e., the photodetector 124--.

Signed and Sealed this
Tenth Day of May, 2016

Michelle K. Lee
*Director of the United States Patent and Trademark Office*

CERTIFICATE OF CORRECTION (continued)
U.S. Pat. No. 9,116,121 B2

In the Specification:

In column 11, lines 19-20, change "the first part with integral an integral elliptical mirrored surface" to --the first part with an integral elliptical mirrored surface--.

In column 11, line 39, change "would be not only be even cheaper" to --would not only be even cheaper--.

In column 11, line 47, change "needs to be air-tight because of the air pressure differential" to --needs to be air-tight because the air pressure differential--.

In the Claims:

In claim 8, column 13, line 3, change "photosensitive detection area is equal or less than 25%" to --photosensitive detection area is equal to or less than 25%--.

In claim 17, column 13, line 33, change "ii) providing a sample of fluid on the form of a flow through" to --ii) providing a sample of fluid in the form of a flow through--.

In claim 18, column 14, line 4, change "i) providing a apparatus as claimed in claim 1;" to --i) providing an apparatus as claimed in claim 1;--.

In claim 22, column 14, line 28, change "signals such that particle detected by both the first" to --signals such that particles detected by both the first--.

In claim 23, column 14, line 37, change "photosensitive detection are is equal to or less that 25%" to --photosensitive detection area is equal to or less than 25%--.